United States Patent [19]
Brimhall et al.

[11] Patent Number: 5,242,393
[45] Date of Patent: Sep. 7, 1993

[54] VALVED BLUNT CANNULA INJECTION SITE

[75] Inventors: Gregory L. Brimhall, West Jordan; Christopher P. Steinman, Sandy; Timothy J. Erskine, Salt Lake City, all of Utah

[73] Assignee: Becton, Dickinson and Company, Franklin Lakes, N.J.

[21] Appl. No.: 900,882

[22] Filed: Jun. 18, 1992

[51] Int. Cl.⁵ .............................................. A61M 5/00
[52] U.S. Cl. ...................................... 604/86; 604/249; 604/283
[58] Field of Search ............. 604/82, 83, 86-88, 604/167, 169, 201, 202, 244, 246, 249, 256, 283, 411, 415, 905

[56] References Cited

U.S. PATENT DOCUMENTS

| | | | |
|---|---|---|---|
| 4,323,065 | 4/1982 | Kling | 128/214 R |
| 4,324,239 | 4/1982 | Gordon et al. | 128/214 R |
| 4,387,879 | 6/1983 | Tauschinski | 604/249 |
| 4,443,219 | 4/1984 | Meisch et al. | 604/256 |
| 4,610,469 | 9/1986 | Wolff-Mooij | 285/260 |
| 4,895,346 | 1/1990 | Steigerwald | 604/167 |
| 4,929,243 | 5/1990 | Koch et al. | 604/283 |
| 4,981,469 | 1/1991 | Whitehouse et al. | 604/86 |
| 5,062,836 | 11/1991 | Wendell | 604/167 |
| 5,078,694 | 1/1992 | Wallace | 604/192 |
| 5,084,032 | 1/1992 | Kornberg et al. | 604/263 |
| 5,085,645 | 2/1992 | Purdy et al. | 604/167 |
| 5,100,394 | 3/1992 | Dudar et al. | 604/283 |

FOREIGN PATENT DOCUMENTS 8906553 7/1989 PCT Int'l Appl. .
9011103 10/1990 PCT Int'l Appl. .

*Primary Examiner*—John D. Yasko
*Assistant Examiner*—Anthony Gutowski
*Attorney, Agent, or Firm*—Michael G. Schwarz

[57] ABSTRACT

An infusion site for infusing fluids into a patient is disclosed. The infusion site has a housing which supports a pre-slit resealable septum which is held in radial compression in the housing. The septum is opened by the insertion of a cannula. The housing also accommodates a valve which is held in tension in the housing and is opened by the insertion of the cannula into the septum. The valve is closed when the cannula is withdrawn. The septum and valve are linked by an elastic member which interacts with the cannula to open and close the valve.

27 Claims, 3 Drawing Sheets

VALVED BLUNT CANNULA INJECTION SITE

BACKGROUND OF THE INVENTION

The invention generally relates to medical infusion devices. In particular, it relates to injection or infusion sites for infusing liquids into a patient.

During the course of medical treatment, it is often necessary to infuse medicinal or nutritional fluids into a patient. It may be necessary to infuse such substances repeatedly or over extended time periods. This is usually done by inserting an indwelling catheter into the body, often the vasculature. Fluids may then be infused repeatedly without the need for repeated piercing of the skin, veins or arteries and the trauma associated with such procedures. Such an indwelling catheter is typically provided with an injection or infusion site which allows a needle or cannula to be inserted and withdrawn as needed so that fluids can be infused through the catheter. Such an injection or infusion site is known as a "PRN" or "pro re nata" (from the Latin for "as the occasion arises") site.

PRN sites are well known in the art. The most commonly used PRN comprises a rubber or silicone septum. Such a PRN is used by penetrating the septum with a hypodermic needle to infuse the fluid. On withdrawal of the needle, the septum reseals itself due to the elasticity of the septum and the fact that the hole made by piercing the septum is very small.

In recent years concern has grown about the risks of infection to health care workers presented by sticks by contaminated needles. Attempts have been made to provide protective shields for needles specifically used for intravenous infusion. U.S. Pat. No. 5,084,032 shows an example of such a system. Another approach is to provide an injection site which shields the nurse or doctor's fingers. An example of this approach is shown in U.S. Pat. No. 5,078,694.

A further approach to avoiding needle sticks resulting from the use of intravenous infusion sets is to use an infusion site having a pre-split septum in conjunction with a blunt cannula rather than one requiring the septum to be pierced by a sharp needle. Examples of this approach are found in International Patent Applications published under the Patent Cooperation Treaty under International Publication Nos. WO 89/06553 and WO 90/11103.

SUMMARY OF THE INVENTION

The invention is a device for facilitating the infusion of fluids into a patient by means of a blunt cannula. The device has a housing for carrying a pre-split septum. Attached to the septum is a valve which is opened by the insertion of a cannula into the septum. The septum re-seals itself and the valve closes when the cannula is withdrawn. Thus two barriers are provided against bacterial and viral infection and the need for a sharp needle is averted.

DETAILED DESCRIPTION

Figure 1:
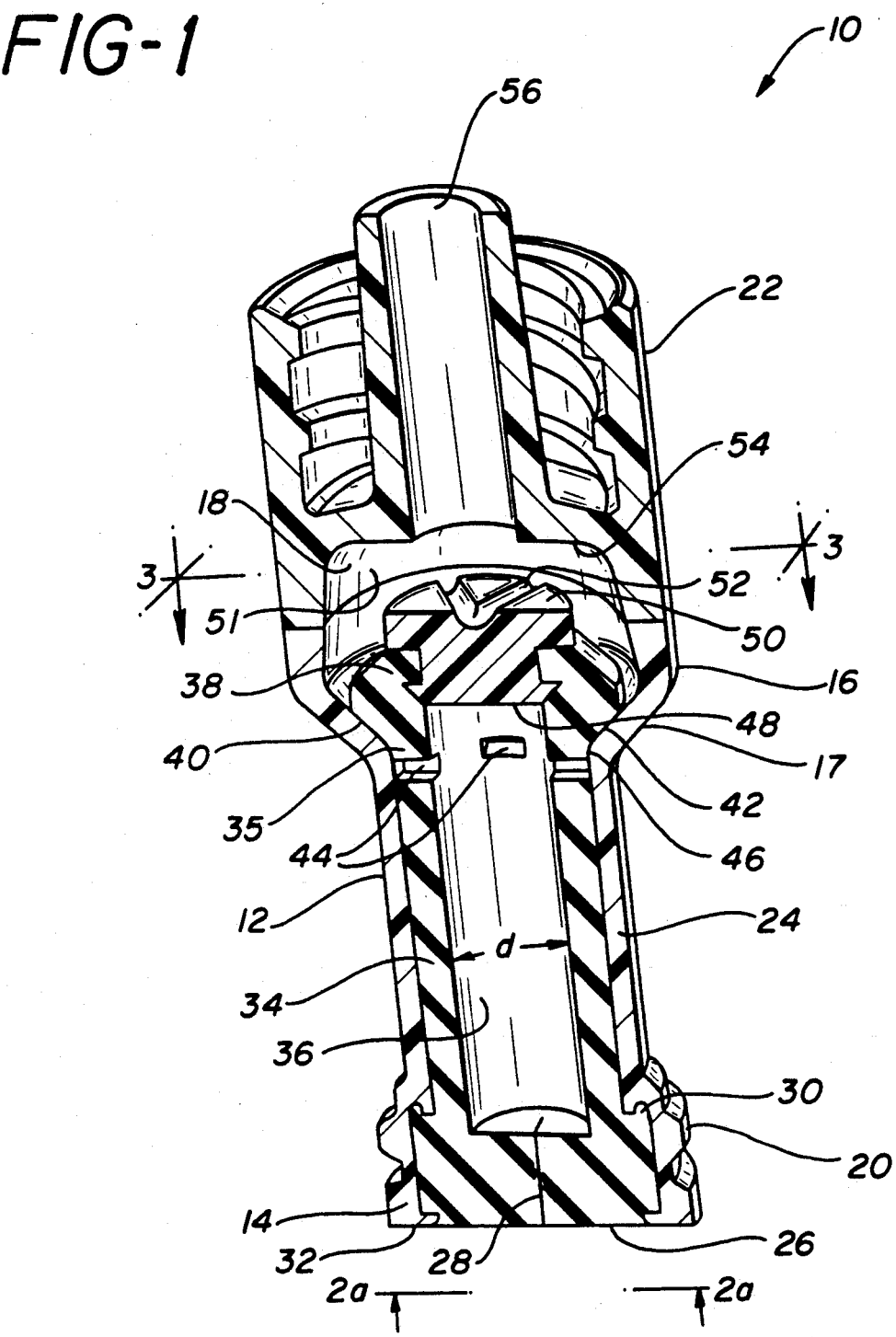
FIG. 1 is a cross-sectional view of the invention prior to the insertion of a cannula.

Valve housing 12 having proximal end 14, distal end 16 and lumen 18 extending between the proximal and distal ends defines the outer casing of device 10. Valve housing 12 is provided with female luer lock type connector 20 at proximal end 14 and male luer type connector 22 at distal end 16. Valve housing 12 and luer type connectors 20 and 22 are injection moulded out of polycarbonate, preferably General Electric Lexan HP ("Health Products") 2. Male luer type connector 22 and valve housing 12 are separately injection molded and then joined preferably by sonic welding. Solvent bonding may also be used to join them. Distal end 16 is slightly enlarged in diameter relative to body section 24 of valve housing 12. Distal end 16 has a generally frusto-conical shaped section 17.

Figure 2A:
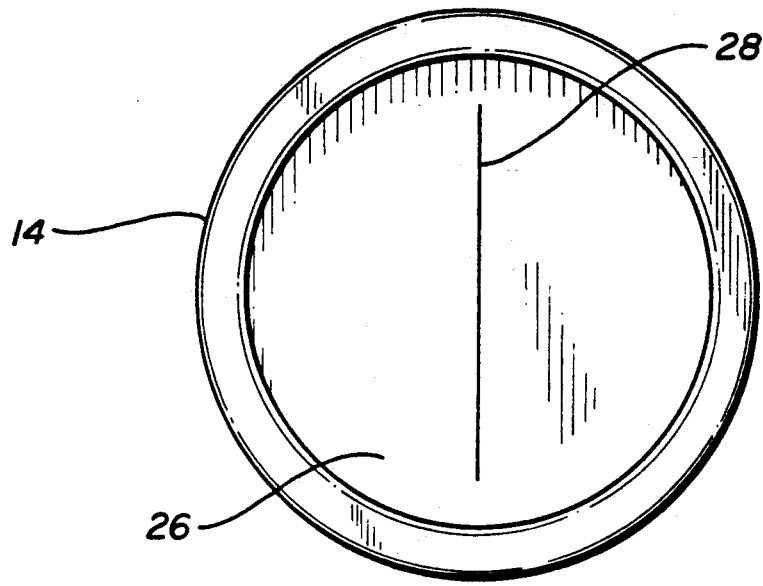
FIG. 2a is a bottom view of the invention showing the slit in the septum viewed from point 2 in FIG. 1.
Figure 2B:
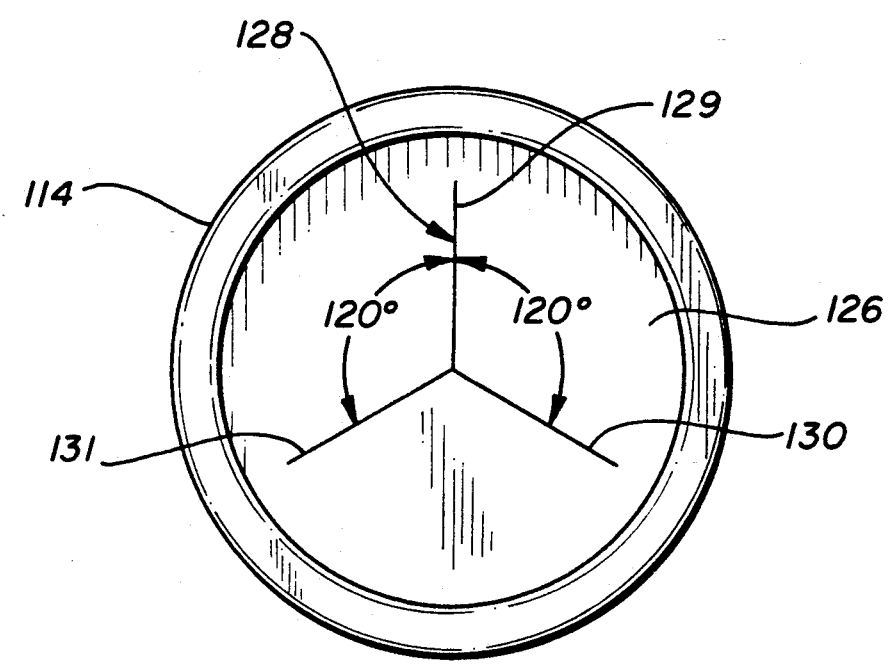
FIG. 2b is a bottom view of an alternative embodiment of the invention having a multi-armed slit in the septum viewed from point 2 in FIG. 1.

Pre split resealable septum 26 is housed at proximal end 14. Septum 26 is provided with slit 28. Slit 28 is shown as a single cut in septum 26 (FIG. 2a), but may be in the form of a multi-armed cut such as a three armed cut 128, the arms 129, 130, 131 being at 120° to each other (FIG. 2b).

Septum 26 is held in place by an interference fit between septum 26 and valve housing 12 at lip 30. Septum 26 provides an anti bacterial seal, preventing the entry of contaminants into valve housing 12. Proximal end 14 may also be provided with flange 32 to hold septum 26 in place. Irrespective of whether septum 26 is held in place by lip 30 or flange 32, septum 26 is held in compression in valve housing 12. The forces exerted by housing 12 on septum 26 are thus directed radially towards the center of septum 26 and cause slit 28 to tend to remain sealed.

Septum 26 is made of an elastically deformable thermoset elastomer, preferably Dow Corning Medical Grade Injection Mouldable silicone rubber available from Dow Corning under product number Q7-4850 (durometer 50 Shore A). Septum 26 is injection molded. The properties of this elastomer are such that slit 28 tends to remain closed unless forced open by the insertion of a cannula or similar object.

Figure 3:
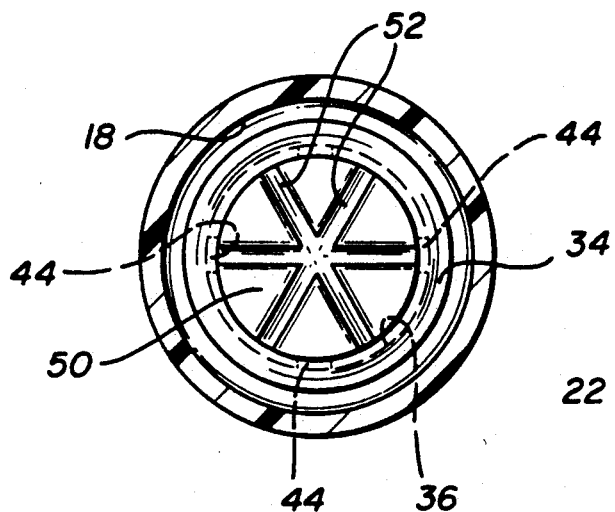
FIG. 3 is a top view of the invention through section 3—3.

Extending towards the distal end 16 of valve housing 12, inside lumen 18 is an elastic extension 34 to septum 26. Extension 34 is preferably integral with and made of the same material as septum 26. Extension 34 defines lumen 36 within lumen 18 of valve housing 12. The walls of extension 34 are dimensioned so that inside diameter d of lumen 36 is slightly smaller than outside diameter D of the tip of cannula 60 (FIG. 3). Extension 34 has a distal end 38. Distal end 38 of extension 34 has a generally frusto-conically shaped section 35 designed to mate with inner surface 40 of frusto conically shaped section 17 of valve housing 12 thereby providing a pressure seal.

Septum 26 and extension 24 are held in tension in valve housing 12 so that distal end 38 tends to push against surface 40, thus keeping surfaces 40 and 42 in sealing engagement. Distal end 38 is provided with valve cap 50 which closes off open end 48 extension 34. Adjacent distal end 38, extension 34 is provided with valve windows 44. As shown in FIG. 1, when surfaces 40 and 42 are in contact, valve windows 44 are closed by wall 46 of valve housing 12. A seal is created by the pressure of surface 40 against surface 42. Thus, a fluid-tight resealable valve is provided between valve housing 12 and extension 34. Valve cap is preferably made of General Electric Lexan HP2 and is held in place at distal end 38 by an interference fit.

Figure 4:
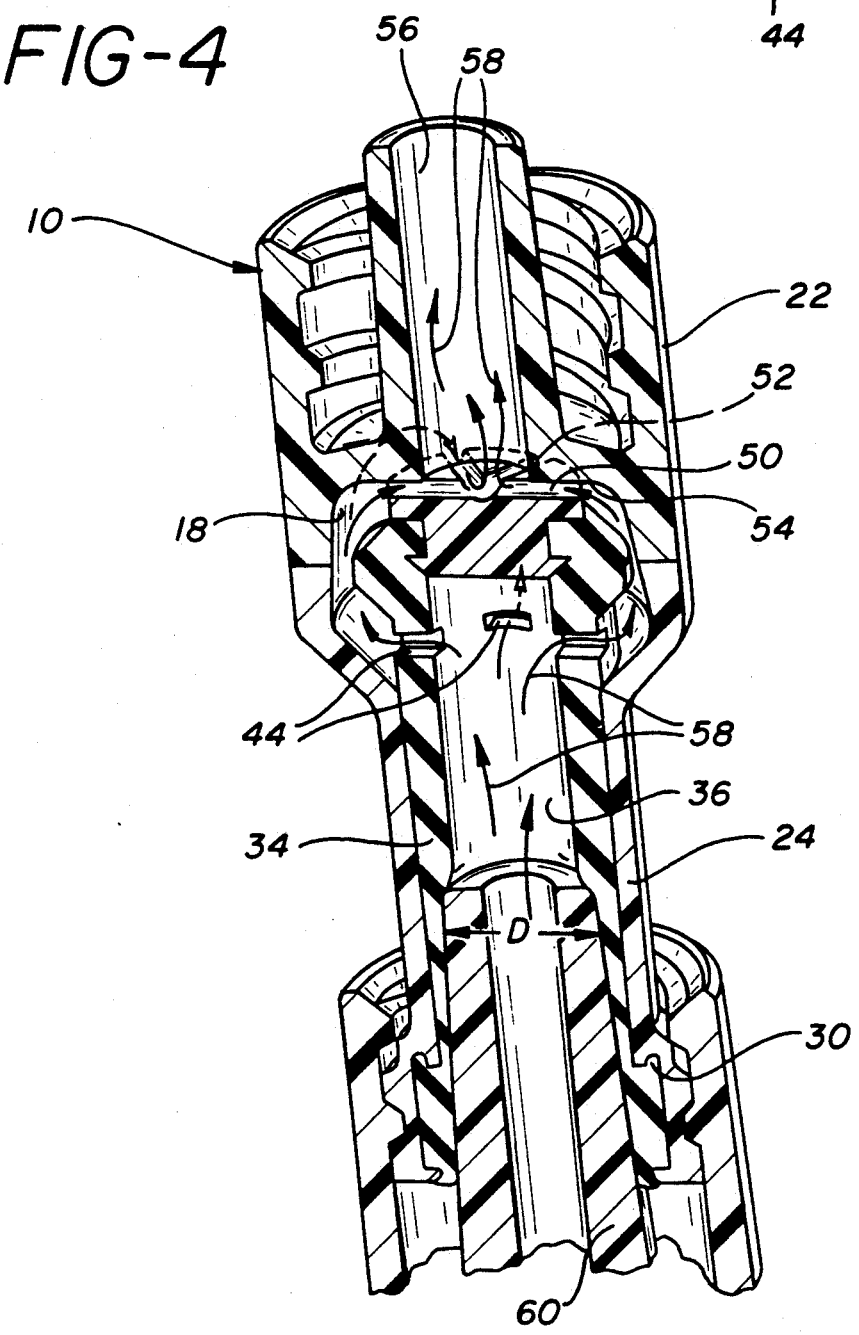
FIG. 4 is a cross-sectional view of the invention showing the septum penetrated by a cannula.

Cannula 60 is shown inserted into septum 26 in FIG. 4. The insertion of cannula 60 splits septum 26 and deforms the material of septum 26. Since septum 26 is constrained by the walls of valve housing 12, and cannula 60 frictionally engages the inner walls of extension 34, the insertion of cannula 60 pushes extension 34 towards distal end 16 of valve housing 12 as shown in FIG. 4. The stretching of extension 34 causes surface 42 of distal end 38 to move out of engagement with surface 40 and causes valve windows 44 to be opened to chamber 52 due to the enlarged diameter of lumen 18 in the region of distal end 16. Once valve windows 44 are opened to chamber 52, fluid can flow from lumen 36 into chamber 52, through lumen 56 and into the patients vasculature as shown by arrows 58 in FIG. 4.

If cannula 60 is inserted sufficiently far into valve housing 12, valve cap 50 will abut surface 54 of luer connector 22. In order to ensure that fluid flows into lumen 56 of luer connector 22, valve cap 50 is provided with fluid channels 52 as shown in FIG. 3.

When cannula 60 is withdrawn, the elasticity of extension 34 and the fact that septum 26 and extension 34 are held in tension in valve housing 12 cause surface 42 of distal end 38 to revert to engagement with surface 40, thus re-closing valve windows 44. When cannula 60 is fully withdrawn, septum 26 will reclose due to the mechanical properties of the material of septum 26 and the fact that septum 26 is radially compressed in housing 12.

We claim:

1. An infusion site for permitting selective infusion of fluid into a patient by means of a blunt cannula, the infusion site comprising:
   a housing having a proximal end, a distal end and a passage therebetween for permitting fluid communication between the proximal end and the distal end;
   an elastically deformable septum supported by the housing and having a re-sealable slit means through which the cannula can be inserted;
   an elastically deformable and stretchable extension to the septum having a proximal end and a distal end, the extension extending at least partially along the length of the housing; and,
   valve means at the distal end of the stretchable extension for opening and closing the passage in the housing, such that the valve means is opened by the insertion of the cannula into the slit means and the frictional engagement of the extension by the cannula, thereby stretching the extension and the valve means is closed when the extension is relaxed on withdrawal of the cannula.

2. The infusion site of claim 1 wherein the stretchable extension is held in tension in the housing with a closing force generally directed towards the proximal end of the housing such that the valve means tends to remain closed unless sufficient force is applied to the extension to overcome the closing force.

3. The infusion site of claim 1 wherein the septum is held in radial compression by the proximal end of the housing such that the slit means tends to remain sealed.

4. The infusion site of claim 1 wherein the extension is dimensioned with respect to the cannula such that the cannula frictionally engages the extension when the cannula is inserted through the slit means, thereby stretching the extension and opening the valve means.

5. The infusion site of claim 1 wherein the housing comprises a luer lock connector at its proximal end.

6. The infusion site of claim 1 wherein the housing comprises a luer lock connector at its distal end.

7. The infusion site of claim 1 wherein the distal end of the stretchable extension comprises a valve plug.

8. The infusion site of claim 7 wherein the valve plug is provided with channels to permit fluid flow.

9. The infusion site of claim 1 wherein the valve means comprises a surface for sealingly engaging the housing.

10. The infusion site of claim 9 wherein the surface is generally frusto-conical.

11. The infusion site of claim 9 wherein the stretchable extension is provided with windows which are open when the valve means is open and closed when the valve means is closed.

12. An infusion site for permitting selective infusion of fluid into a patient by means of a blunt cannula, the infusion site comprising:
    a housing having a proximal end and a distal end and a passage therebetween;
    a septum supported by the housing at the proximal end of the housing, the septum having a re-sealable slit means for permitting entry of the cannula;
    valve means for selectively permitting fluid flow through the passage; and,
    actuating means actuable by entry of the cannula into the slit means for opening and closing the valve means, the actuating means being connected to the septum and being actuable by insertion of the cannula into the septum.

13. The infusion site of claim 12 wherein the actuating means for opening and closing comprise an elastic member connecting the valve means to the septum.

14. The infusion site of claim 13 wherein the elastic member is dimensioned relative to the cannula so that the cannula frictionally engages at least part of the elastic member on insertion of the cannula into the slit means, thereby opening the valve means.

15. The infusion site of claim 13 wherein the elastic member is housed in the housing.

16. The infusion site of claim 12 wherein the septum is held in radial compression in the housing.

17. The infusion site of claim 13 wherein the elastic member is held in tension in the housing.

18. A system for infusion of fluids into a patient, the system comprising:
    a blunt cannula;
    a housing comprising a proximal end and a distal end and a passage connecting therebetween for permitting fluid flow;
    a septum secured to the proximal end of the housing, and having a resealable slit therein, the septum being sealingly penetrable by insertion of the cannula into the slit;
    valve means disposed between the septum and the distal end of the housing for controlling fluid flow through the passage, the valve means being connected to the septum and wherein the valve means is opened by the penetration of the septum by the cannula and closed on withdrawal of the cannula from the septum; and,
    a stretchable extension to the septum, the extension extending from the septum toward the distal end of the housing and the extension being stretched by the penetration of the septum by the cannula thereby opening the valve means and the septum being relaxed on withdrawal of the cannula from the septum, thereby closing the valve means.

19. The system of claim 18 wherein the stretchable extension is held in tension in the housing with a closing force generally directed towards the proximal end of the housing such that the valve means tends to remain closed unless sufficient force is applied to the extension to overcome the closing force.

20. The infusion site claim 18 wherein the septum is held in radial compression by the proximal end of the housing such that the slit means tends to remain sealed.

21. The infusion site of claim 18 wherein the extension is dimensioned with respect to the cannula such that the cannula is inserted into the slit means, thereby stretching the extension and opening the valve means.

22. The infusion site of claim 18 wherein the housing comprises a luer connector at its proximal end.

23. The infusion site of claim 18 wherein the housing comprises a luer connector at its distal end.

24. The infusion site of claim 18 wherein the distal end of the stretchable extension comprises a valve plug.

25. The infusion site of claim 18 wherein the valve means is provided with channels to permit fluid flow.

26. The infusion site of claim 18 wherein the valve means comprises a surface for sealingly engaging the housing.

27. The system of claim 18 wherein the extension is disposed within the housing.

* * * * *